(12) United States Patent
Dufau et al.

(10) Patent No.: US 6,849,276 B1
(45) Date of Patent: Feb. 1, 2005

(54) LIQUID COMPOSITION WITH FUNGICIDE, BACTERICIDAL AND BACTERIOSTATIC ACTIVITY

(75) Inventors: Ghislain Dufau, Dax (FR); Michel Barsacq, Dax (FR); Gérard Molla, Dax (FR)

(73) Assignee: Action Pin, Dax (FR)

( * ) Notice: Subject to any disclaimer, the term of this patent is extended or adjusted under 35 U.S.C. 154(b) by 0 days.

(21) Appl. No.: 09/830,358

(22) PCT Filed: Aug. 24, 1999

(86) PCT No.: PCT/FR99/02036

§ 371 (c)(1),
(2), (4) Date: Apr. 25, 2001

(87) PCT Pub. No.: WO00/24259

PCT Pub. Date: May 4, 2000

(30) Foreign Application Priority Data

Oct. 26, 1999 (FR) .............................. 98 13381

(51) Int. Cl.⁷ ................... A01N 59/20; A01N 65/00; A01N 25/30; A01N 55/02
(52) U.S. Cl. .................... 424/633; 424/405; 424/604; 424/630; 424/631; 424/632; 424/634; 424/635; 424/637; 424/638; 424/725; 424/769; 424/770; 514/675; 514/690; 514/693; 514/703; 514/714; 514/715; 514/724; 514/729; 514/739; 514/762; 514/763; 514/766; 514/783; 514/937; 514/938; 514/951; 514/975

(58) Field of Search .................. 424/604, 405, 424/630–635, 637–638, 725, 769, 770; 514/675, 690, 693, 703, 714, 715, 724, 729, 739, 762, 763, 766, 783, 937, 938, 951, 975

(56) References Cited

U.S. PATENT DOCUMENTS 3,592,910 A * 7/1971 Clark et al. .................. 514/481
6,069,113 A * 5/2000 Kierzkowski et al. ....... 504/152

FOREIGN PATENT DOCUMENTS

EP 0 517 569 12/1992
WO 95/07807 3/1995
WO 98/31223 * 7/1998

OTHER PUBLICATIONS

Farm Chemicals Handbook '98, Meister Publishing Co., Willoughby, OH, vol. 84, pp. C100–C104.*

* cited by examiner

Primary Examiner—John Pak
(74) Attorney, Agent, or Firm—Wenderoth, Lind & Ponack, L.L.P.

(57) ABSTRACT

The invention concerns a phytosanitary fungicide, bactericidal or bacteriostatic composition comprising at least a mineral salt, a copper oxide or hydroxide suspended in an aqueous emulsion of at least a terpene derivative.

18 Claims, No Drawings

LIQUID COMPOSITION WITH FUNGICIDE, BACTERICIDAL AND BACTERIOSTATIC ACTIVITY

This application is a 371 application of PCT/FR99/02036, filed Aug. 24, 1999.

The subject of the present invention is a liquid composition with fungicidal, bacteriostatic or bactericidal activity, and methods for the preparation and use of the composition.

It has long been known to use phytopharmaceutical products based on inorganic salts, oxides or hydroxides of copper, in particular for their fungicidal properties (vine downy mildew and the like) but also for their bactericidal power (bacterial canker of peach and apricot trees, bacteriosis of apple and pear trees caused by pseudomonas, and the like) or their bacteriostatic power which prevents bacterial diseases from becoming established.

The fungicidal and bactericidal activity of copper depends on the nature of the copper compound and on the quality of its manufacture.

The "Bordeaux mixture" has been used for over a century for the treatment of grape vine. First prepared by the viticulturist, and then manufactured industrially, it is obtained by accurately neutralizing a solution of copper sulfate with a milk of lime. This mixture, brought to neutrality (pH=7) is then dried, ground and micronized.

Among the other products based on copper, there may be mentioned copper oxichloride, copper hydroxide, copper carbonate, copper(I) oxide, and the like.

These inorganic salts, oxides or hydroxides of copper, used alone or in combination with other compounds, are generally provided in the form of wettable powders, dispersible granules, suspension concentrates, dustable powders, and the like.

The inorganic salts, oxides or hydroxides of copper may also be combined with inorganic fungicides, in particular sulfur, or organic fungicides to form, in the latter case, organocopper compounds.

Among the organic active substances, there may be mentioned in particular folpel, maneb, mancozeb, propineb, zineb, cymoxanil, metiram-zinc.

The formulations are provided in the forms described above.

With the exception of the dustable powders, the other compositions generally comprise surfactants, wetting agents, dispersing agents, emulsifiers, antifoams and the like, which contribute to the stability of the formulations and then to the use of the products, and in particular to their dispersion in water for the production of mixtures for treatment.

In addition to the choice of inorganic salts, oxides or hydroxides of copper and to the selection of surfactants, formulators seek to enhance the efficacy of the products because the degree of protection from a copper compound against attacks by fungi and bacteria is closely related to its capacity to saturate the surface of the plant by forming a microscopic film of particles. Adherence to the plant followed by resistance to strong rain is also one of the objectives sought by the manufacturers.

For some time now, and in particular for the treatment of grape vine, many products using copper hydroxide as active substance have been appearing on the market.

The optimization of the formulations based on copper hydroxide, in particular of the suspension concentrates, has been carried out by:

the search for a specific structure for the particles: crystallized fine needles, acicular structure;

the improvement in the reduction of their size obtained by micronization or by a chemical method for manufacture of copper hydroxide, it being possible for said size to reach from 0.3 to 0.4 μm;

the choice of the surfactants and co-formulants capable of stabilizing the formulation and of increasing the efficacy thereof.

FR 2 599 592 describes liquid formulations for the preventive and curative treatment of cryptogamic diseases of the oidium type comprising a lipophilic inorganic active substance consisting of fine ground or micronized sulfur, in suspension in a liquid composed of a mixture of pine oil and water, the pine oil enhancing the efficacy of the sulfur.

The work by the inventors which has led to the present invention has made it possible to establish that the efficacy of inorganic salts, oxides or hydroxides of copper can, surprisingly, be enhanced when these were combined with a terpenic derivative.

This discovery is unexpected insofar as persons skilled in the art did not expect the efficacy of inorganic salts, oxides or hydroxides of copper to be enhanced by the addition of terpenic derivatives because of the difference in physicochemical nature between the inorganic salts, oxides or hydroxides of copper, on the one hand, and the sulfur metal species, on the other hand, in particular because of the fact that sulfur is essentially lipophilic, while the inorganic salts, oxides or hydroxides of copper are essentially hydrophilic.

The subject of the invention is a fungicidal, bactericidal or bacteriostatic plant-protection composition comprising at least one inorganic salt, one oxide or one hydroxide of copper in suspension in an aqueous emulsion of at least one terpenic derivative.

The aqueous emulsions also cover the microemulsions.

The inorganic salt, oxide or hydroxide of copper consists of one or of a mixture of those mentioned above, copper hydroxide ($Cu(OH)_2$) being preferred.

The terpenic derivatives for the purposes of the present invention are organic molecules containing ten carbon atoms in their structure.

They are therefore essentially monoterpenes.

The terpenic derivatives may be acyclic, monocyclic or bicyclic.

The following examples may be mentioned in particular:
1) the terpenic hydrocarbons:
a) acyclic terpenic hydrocarbons: myrcene, alloocimene, and the like;
b) monocyclic terpenic hydrocarbons: dipentene, terpinolene, p-cymene, limonene, and the like;
c) bicyclic terpenic hydrocarbons: α-pinene, β-pinene or δ-3-carene, and the like;
2) the following compounds:
a- the oxidized derivatives; cineols;
b- the terpenic alcohols: borneol, fenchol, menthanol, terpineols, geraniol, 1-terpinen-4-ol, and the like;
c- the aldehydes and ketones: camphor, fenchone;
3) the mixtures of the products cited above;
4) the essential oils containing the above mixtures in various proportions, for example Malalenca alternifolia essential oil (or tea-tree oil);
5) the pine oils of natural or synthetic origin which are defined as being mixtures of terpenic hydrocarbons and alcohols.

Pine oil containing 90% of terpenic alcohols is most particularly preferred.

The suspension according to the invention advantageously also contains at least one surfactant for its emulsifying, wetting, crystal growth inhibiting properties, and the like.

It is possible to use an anionic, cationic, amphoteric, zwitterionic and/or nonionic surfactant.

The anionic and nonionic surfactants, alone or in the form of a mixture, are preferred.

The following compounds are particularly well suited to the aim of the invention:

ethoxylated fatty acids,
ethoxylated fatty alcohols,
calcium alkylbenzenesulfonate,
alkylnaphthalenesulfonates,
ethoxylated alkylphenols,
EO/PO block copolymers,
PO/EO block copolymers,
diisopropylnaphthalenesulfonates,
dimethylnaphthalenesulfonates,
di-n-butylnaphthalenesulfonates,
ethoxylated dodecylphenols,
sodium dodecylbenzenesulfonate,
phosphoric esters of alkyl polyethers (acid forms and/or salts),
phosphoric esters of ethoxylated arylphenols (acid forms and/or salts),
phosphoric esters of ethoxylated polyarylphenols (acid forms and/or salts),
ethoxylated castor oil,
isopropylnaphthalenesulfonates,
lignosulfonates,
methyldinapthalenesulfonates,
methylnaphthalenesulfonates,
n-butylnapthalenesulfonates,
ethoxylated octylphenols,
phenyl sulfonates,
polyalkylnaphtylmethanesulfonates,
polyacrylates,
ethoxylated polyarylphenols,
polycarboxylates,
polyvinylpyrrolidone and derivatives thereof,
salts of sulfonated cresol-formalin condensates,
salts of condensates of naphthalenesulfonic acid,
salts of acrylic acid-acrylic ester copolymers,
salts of maleic acid-olefin copolymers,
salts of maleic anhydride-isobutylene copolymers,
ethoxylated alkylphenol sulfates,
ethoxylated polyarylphenol sulfates,
sulfosuccinates,
taurates,
ethoxylated tristyrylphenols . . .

The suspension concentrates of the present invention advantageously comprise from 200 to 600 g/l, preferably 300 to 500 g/l of copper, of the inorganic salt, oxide or hydroxide of copper expressed relative to the copper element. The contents of terpenes in the formulations are between 50 and 400 g/l, preferably 80 to 200 g/l.

The contents of surfactant(s) in the formulations are between 20 and 100 g/l, preferably 30 to 60 g/l.

The liquid compositions of the invention, also called suspension concentrates or "flowable concentrates" may be prepared by micronizing the active substance, optionally mixed with a portion or all of the other ingredients, by passing through a specific mill (for example a ball mill of the ®DYNO-MILL type) until a stable homogeneous suspension is obtained.

Mechanical micronization may be avoided and a simple mixing may be sufficient if an active substance which is already micronized either mechanically or by the method of synthesis, is used. In either case, the micronization is performed until a diameter of the particles of inorganic salts, oxides or hydroxides of copper not greater than 6 µm is obtained.

An example of copper hydroxide which may be suitable for the preparation of a composition by simple mixing is the technical copper hydroxide manufactured by NORDEUTSCHE AFFINERIE, marketed by URANIA AGROCHEM GmbH.

It is also possible to use a copper hydroxide prepared in accordance with the methods described in U.S. Pat. No. 3,194,749 and U.S. Pat. No. 4,944,935.

The compositions of the invention have a markedly improved fungicidal, bactericidal or bacteriostatic activity compared with the compositions of the state of the art not containing a terpenic derivative.

This gain in efficacy makes it possible to reduce the quantities of copper applied to the plants during treatments.

This dose reduction is very advantageous because it makes it possible to reduce the sometimes depressive action which copper exerts on plants and its phytotoxicity toward some plants.

The subject of the invention is also the use of a terpenic derivative for enhancing the efficacy of an inorganic salt, an oxide or a hydroxide of copper in a plant-protection, in particular fungicidal, bactericidal or bacteriostatic, composition.

The subject of the invention is, furthermore, a method of treating plants with a product based on an inorganic salt, oxide or hydroxide of copper, characterized in that an effective quantity of plant-protection mixture prepared by mixing, in aqueous form, a composition of an inorganic salt, oxide or hydroxide of copper in suspension in an aqueous emulsion containing at least one terpenic derivative, is sprayed on the plant to be treated.

Examples of compositions based on an inorganic salt, oxide or hydroxide of copper and a terpene according to the invention as well as the results obtained with these compositions on vine downy mildew (*Plasmopara viticola*) will be given below.

EXAMPLES 1 TO 3 OF COMPOSITIONS ACCORDING TO THE INVENTION

|  | Formula A | | Formula B | | Formula C | |
|---|---|---|---|---|---|---|
|  | Content of copper: from 300 to 310 g/l | | | | | |
| Copper hydroxide | 36.76% | 501 g/l | 36.76% | 500 g/l | 36.76% | 500 g/l |
| Pine oil (containing 90% of terpenic alcohols) | 6.60% | 90 g/l | 9.78% | 133 g/l | 12.94% | 176 g/l |
| Urea | 4.00% | 54.5 g/l | 4.00% | 54.4 g/l | 4.00% | 54.4 g/l |
| TENSIOFIX ® BCZ (sulfated alcohol) | 1.00% | 13.6 g/l | 1.00% | 13.6 g/l | 1.00% | 13.6 g/l |

-continued

|  | Formula A | | Formula B | | Formula C | |
| --- | --- | --- | --- | --- | --- | --- |
| | Content of copper: from 300 to 310 g/l | | | | | |
| TENSIOFIX ® LX (lignosulfonate) | 1.00% | 13.6 g/l | 1.00% | 13.6 g/l | 1.00% | 13.6 g/l |
| TENSIOFIX ® D40 (cationic/nonionic surfactant) | 1.00% | 13.6 g/l | 1.00% | 13.6 g/l | 1.00% | 13.6 g/l |
| Silcone-containing antifoam | 0.05% | 0.7 g/l | 0.05% | 0.7 g/l | 0.05% | 0.7 g/l |
| BARAGEL ® 24 | 1.50% | 20.5 g/l | 1.00% | 13.6 g/l | 0.50% | 6.8 g/l |
| Water | 48.09% | 656.1 g/l | 45.41% | 617.5 g/l | 42.75% | 581.4 g/l |

Active substance: Technical copper hydroxide (content of copper: 62.05%)

Composition prepared by mixing the various ingredients and then micronizing by passing through a mill of the ®DYNO-MILL type.

TENSIOFIX®: OMNICHEM trademark

BARAGEL®: NL-CHEMICAL trademark.

EXAMPLE 4

Example of Composition According to the Invention

|  | Formula D | |
| --- | --- | --- |
| | Content of copper: 396.1 g/l | |
| Copper hydroxide | 43.55% | 659 g/l |
| Pine oil (containing 90% of terpenic alcohols) | 8.62% | 130.5 g/l |
| Polyarylphenol phosphate which is ethoxylated and neutralized with triethanolamide | 1.67% | 25.3 g/l |
| Aqueous solution containing 35% of a sodium salt of a sulfonated cresol-formalin condensate | 4.91% | 74.3 g/l |
| Monoethylene glycol | 5.84% | 88.4 g/l |
| Heteropolysaccharide of the xanthan gum type | 0.11% | 1.7 g/l |
| Silicone-containing antifoam | qs | qs |
| Water | qs 100 | qs 100 |

Active substance: Technical copper hydroxide (content of copper=62.4%) marketed by URANIA AGROCHEM GmbH Particle Size
<13 μm: 100%
<6.6 μm: 92.4%
<4.7 μm: 81.5%
<3.3 μm: 64.8%
<2.4 μm: 47.6%

Composition prepared by simple mixing of the various ingredients.

EXAMPLE 5

Example of Composition According to the Invention

|  | Formula E | |
| --- | --- | --- |
| | Content of copper: 407 g/l | |
| Copper hydroxide | 45.00% | 619.2 g/l |
| Pine oil (containing 90% of terpenic alcohols) | 7.80% | 119.8 g/l |

-continued

|  | Formula E | |
| --- | --- | --- |
| | Content of copper: 407 g/l | |
| Polyarylphenol phosphate which is ethoxylated and neutralized with triethanolamine | 2.20% | 33.8 g/l |
| Aqueous solution containing 35% of a sodium salt of a sulfonated cresol-formalin condensate | 5.00% | 76.8 g/l |
| Glycerol | 1.40% | 21.5 g/l |
| Urea | 6.00% | 92.2 g/l |
| Silicone-containing antifoam | qs | qs |
| Heteropolysaccharide of the xanthan gum type | 0.125% | 1.9 g/l |
| Water | qs 100 | qs 100 |

Active substance: Technical copper hydroxide (content of copper=62.88%)

Composition prepared by mixing the various ingredients and then micronizing by passing through a ball mill of the ®DYNO-MILL type.

EXAMPLE 6

Results of Experimentation on Vine Downy Mildew (*Plasmopara viticola*)

1st Trial: Scores on Leaves

|  | Dose/ha of Product | Doses/ha | | % of damage on leaves | |
| --- | --- | --- | --- | --- | --- |
|  |  | Copper | Pine oil | 1st score | 2nd score |
| NTC | / | / | / | 68.75% | 97.50% |
| Formula B | 5 l | 1500 g | 665 g | 43.75% | 83.75% |
| Formula C | 5 l | 1500 g | 880 g | 40.63% | 84.38% |
| Formula A | 7.5 l | 2250 g | 675 g | 43.13% | 85.63% |
| Formula B | 7.5 l | 2250 g | 998 g | 29.38% | 70.63% |
| Formula C | 7.5 l | 2250 g | 1320 g | 26.25% | 68.13% |
| SC formulation (state of the art) | 8.8 l | 3000 g | / | 38.13% | 82.50% |
| WP formulation (state of the art) | 6 kg | 3000 g | / | 42.50% | 78.13% |

Study on young plants

Grape vine, Cabernet-Sauvignon cultiver

Trials under misting with artificial contaminations

NTC: Non treated control SC: Suspension concentrate

WP: Wettable powder

2nd Trial: Scores on Bunches of Grapes

|  | Dose/ha of Product | Doses/ha Copper | Pine oil | 1st score Intensity | Frequency | 2nd score Intensity | Frequency |
|---|---|---|---|---|---|---|---|
| NTC | / | / | / | 72.85% | 14.29% | 98.20% | 58.56% |
| Formula D | 5 l | 2050 g | 650 g | 6.41% | 0.33% | 27.50% | 2.29% |
| SC formulation (state of the art) | 6.7 l | 2030 g | / | 9.09% | 0.75% | 36.03% | 2.82% |

Study on fruit-bearing plants
Grape vine, Cabernet-Sauvignon cultiver
Trials under misting with artificial contaminations
NTC: Non treated control SC: Suspension concentrate 3rd Trial: Scores on Leaves

|  | Dose/ha of Product | Doses/ha Copper | Pine oil | % of damage on leaves | % of defoliating |
|---|---|---|---|---|---|
| Formula D | 5 l | 2050 g | 650 g | 22.50% | 48.75% |
| SC formulation (state of the art) | 6.7 l | 2030 g | / | 36.25% | 60.00% |

Study on fruit-bearing plants
Grape vine, Cabernet-Sauvignon cultiver
Trials under misting with artificial contaminations
SC: Suspension concentrate 4th Trial: Scores on Leaves

|  | Dose/ha of Product | Doses/ha Copper | Pine oil | 1st score Intensity | Frequency | 2nd score Intensity | Frequency | 3rd score Intensity | Frequency |
|---|---|---|---|---|---|---|---|---|---|
| NTC | / | / | / | 15.0% | 64.5% | 62.83% | 99.0% | 58.65% | 84.0% |
| Formula E | 4 1 | 1630 g | 480 g | 1.8% | 6.8% | 1.63% | 16.0% | 1.47% | 14.3% |
| Formula E | 5 1 | 2040 g | 600 g | 1.5% | 6.8% | 0.90% | 9.0% | 1.33% | 15.0% |
| Formula E | 6.25 1 | 2540 g | 750 g | 2.2% | 8.5% | 1.22% | 11.5% | 1.16% | 11.0% |
| SC formulation (state of the art) | 7 1 | 2520 g | / | 2.0% | 8.8% | 2.20% | 19.0% | 1.91% | 15.3% |

Study on fruit-plants
Grape vine, Grenache
Trials under misting with atificial contaminations
NTC: Non treated control SC: Suspension concentrate 5th Trial: Scores on Bunches of Grapes

|  | Dose/ha of Product | Doses/ha Copper | Pine oil | 1st score Intensity | Frequency | 2nd score Intensity | Frequency |
|---|---|---|---|---|---|---|---|
| NTC | / | / | / | 9.90% | 57.5% | 67.70% | 99.8% |
| Formula E | 4 1 | 1630 g | 480 g | 0.20% | 2.3% | 7.05% | 42.8% |
| Formula E | 5 1 | 2040 g | 600 g | 0.15% | 2.6% | 7.30% | 36.3% |
| Formula E | 6.25 1 | 2540 g | 750 g | 0.01% | 0.5% | 1.70% | 14.8% |
| SC formulation (state of the art) | 7 1 | 2520 g | / | 9.09% | 1.5% | 4.10% | 29.5% |

Study on fruit-bearing plants

Grape vine, Grenache

Trials under misting with artificial contaminations

NTC: Non treated control SC: Suspension concentrate

6th Trial: Scores on Leaves

|  | Dose/ha of Product | Doses/ha Copper | Pine oil | 1st score Intensity | Frequency | 2nd score Intensity | Frequency | 3rd score Intensity | Frequency |
|---|---|---|---|---|---|---|---|---|---|
| NTC | / | / | / | 24.3% | 84.5% | 27.83% | 97.8% | 27.34% | 91.8% |
| Formula E | 4 l | 1630 g | 480 g | 0.6% | 3.5% | 0.90% | 4.5% | 0.35% | 2.3% |
| Formula E | 5 l | 2040 g | 600 g | 0.2% | 2.3% | 0.23% | 2.3% | 0.17% | 1.3% |
| SC formulation (state of the art) | 7 l | 2520 g | / | 0.2% | 2.0% | 0.45% | 2.0% | 0.18% | 2.0% |

Study on fruit-bearing plants
Grape vine, Grenache
Trials under misting with artificial contaminations
NTC: Non treated control SC: Suspension concentrate
17th Trial: Scores on Bunches of Grapes

|  | Dose/ha of Produce | Doses/ha Copper | Pine oil | Intensity | Frequency |
|---|---|---|---|---|---|
| NTC | / | / | / | 6.5% | 39.8% |
| Formula E | 4 l | 1630 g | 480 g | 0.1% | 0.8% |
| Formula E | 5 l | 2040 g | 600 g | 0.1% | 0.4% |
| Formula E | 6.25 l | 2540 g | 750 g | 0.0% | 0.4% |
| SC formulation (state of the art) | 7 l | 2520 g | / | 0.1% | 0.9% |

Study on fruit-bearing plants
Grape vine, Grenache
Trials under misting with artificial contaminations
NTC: Non treated control SC: Suspension conentrate

What is claimed is:

1. A fungicidal, bactericidal or bacteriostic plant-protection composition comprising at least one inorganic salt, one oxide or one hydroxide of copper in suspension in an aqueous emulsion of at least one monoterpene.

2. The composition of claim 1, wherein said inorganic salt, oxide or hydroxide of copper is selected from the group consisting of copper hydroxide, copper oxychloride, copper carbonate, copper(I) oxide and mixtures thereof.

3. The composition of claim 1, wherein said inorganic salt, oxide or hydroxide of copper is copper hydroxide.

4. The composition of claim 1, wherein copper is present from 200 to 600 g/l, in the form of an inorganic salt, oxide or hydroxide of copper.

5. The composition of claim 1, wherein the diameter of the particles of said inorganic salt, oxide or hydroxide of copper is not greater than 6 µm.

6. The composition of claim 1, wherein said monoterpene is selected from the group consisting of terpenic hydrocarbons, oxidized derivatives of terpenic hydrocarbons, terpenic alcohols, terpenic aldehydes and ketones and mixtures thereof.

7. The composition of claim 1, wherein said monoterpene is a mixture of terpenic hydrocarbons and terpenic alcohols.

8. The composition of claim 1, wherein said monoterpene is an essential oil.

9. The composition of claim 1, wherein said monotermene is a pine oil.

10. The composition of claim 1, wherein said monoteroene is a pine oil containing 90% by weight of terpenic alcohols.

11. The composition of claim 1, wherein said at least one monoterpene is (are) present from 50 to 400 g/l.

12. The composition of claim 1, further comprising at least one surfactant.

13. The composition of claim 1, further comprising from 20 to 100 g/l of surfactant(s).

14. The composition of claim 1, further comprising a surfactant selected from the group consisting of:
   ethoxylated fatty acids,
   ethoxylated fatty alcohols,
   calcium alkylbenzenesulfonate,
   alkylnaphthalenesulfonates,
   ethoxylated alkylphenols,
   EO/PO block copolymers,
   PO/EO block copolymers,
   diisopropyinaphthalenesulfonates,
   dimethylnaphthalenesulfonates,
   di-n-butylnaphthalenesulfonates,
   ethoxylated dodecylphenols,
   sodium dodecylbenzenesulfonate,
   phosphoric esters of alkyl polyethers (acid forms and/or salts),
   phosphoric esters of ethoxylated arylphenols (acid forms and/or salts),
   phosphoric esters of ethoxylated polyarylphenols (acid forms and/or salts),
   ethoxylated castor oil,
   isopropylnaphthalenesulfonates,
   lignosulfonates,
   methyldinapthalenesulfonates,
   methylnaphthalenesulfonates,
   n-butylnapthalenesulfonates,
   ethoxylated octylphenols,
   phenyl sulfonates,
   polyalkylnaphtylmethanesulfonates,
   polyacrylates,
   ethoxylated polyarylphenols,
   polyvinylpyrrolidone and derivatives thereof,
   salts of sulfonated cresol-formalin condensates,
   salts of condensates of naphthalenesulfonic acid,
   salts of acrylic acid-acrylic ester copolymers,
   salts of maleic acid-olefin copolymers,
   salts of maleic anhydride-isobutylene copolymers,
   ethoxylated alkylphenol sulfates,
   ethoxylated polyarylphenol sulfates,
   sulfosuccinates,
   taurates, and
   ethoxylated tristyrylphenols.

15. A method of preparing a fungicidal, bactericidal or bacteriostic plant-protection composition comprising at least one inorganic salt, one oxide or one hydroxide of copper in suspension in an aqueous emulsion of at least one monoterpene, comprising micronizing said inorganic salt, oxide or hydroxide of copper and other ingredients of the composition comprising at least one monoterpene, water and at least one surfactant until a stable homogeneous suspension is obtained in which the size of the particles is less than 6 μm.

16. A method of preparing a fungicidal, bactericidal or bacteriostic plant-protection composition comprising at least one inorganic salt, one oxide or one hydroxide of copper in suspension in an aqueous emulsion of at least one terpenic derivative, comprising admixing said inorganic salt, oxide or hydroxide of copper, having a diameter not greater than 6 μm, with other ingredients of the composition comprising at least one terpenic derivative, water and at least one surfactant until a stable homogeneous suspension is obtained.

17. A method of enhancing the efficacy of an inorganic salt, oxide or hydroxide of copper in a plant-protection composition, comprising combining said inorganic salt, oxide or hydroxide of copper in suspension in an aqueous emulsion with at least one monoterpene.

18. A method of treating plants with a product based on an inorganic salt, oxide or hydroxide of copper, comprising spraying an effective quantity of a plant-protection mixture prepared by mixing, in aqueous form, a composition of an inorganic salt, oxide or hydroxide of copper in suspension in an aqueous emulsion containing at least one monoterpene, on the plant to be treated.

* * * * *

UNITED STATES PATENT AND TRADEMARK OFFICE
CERTIFICATE OF CORRECTION

PATENT NO. : 6,849,276 B1
DATED : February 1, 2005
INVENTOR(S) : Ghislain Dufau et al.

It is certified that error appears in the above-identified patent and that said Letters Patent is hereby corrected as shown below:

Title page,
Item [54], Title, change "FUNGICIDE" to -- FUNGICIDAL --.
Item [30], Foreign Application Priority Data, change "Oct. 26, 1999" to -- Oct. 26, 1998 --.

Signed and Sealed this

Twenty-fourth Day of May, 2005

JON W. DUDAS
*Director of the United States Patent and Trademark Office*